United States Patent  
Vilkomerson

Patent No.: US 6,726,628 B2  
Date of Patent: Apr. 27, 2004

(54) ANGLE-INDEPENDENT DOPPLER SYSTEM FOR SCREENING

(75) Inventor: David Vilkomerson, Princeton, NJ (US)

(73) Assignee: DVX, LLC, Princeton, NJ (US)

( * ) Notice: Subject to any disclaimer, the term of this patent is extended or adjusted under 35 U.S.C. 154(b) by 0 days.

(21) Appl. No.: 10/430,124

(22) Filed: May 6, 2003

(65) Prior Publication Data

US 2003/0212329 A1 Nov. 13, 2003

Related U.S. Application Data

(60) Provisional application No. 60/378,515, filed on May 7, 2002.

(51) Int. Cl.⁷ ................................................ A61B 8/00
(52) U.S. Cl. ........................................ 600/454; 600/457
(58) Field of Search ................................ 600/454, 443, 600/447, 451, 455, 453, 457; 702/159; 73/170.03, 861.25, 861.26

(56) References Cited

U.S. PATENT DOCUMENTS

| | | | | |
|---|---|---|---|---|
| 4,062,237 | A | | 12/1977 | Fox .......................... 73/194 A |
| 5,454,372 | A | * | 10/1995 | Banjanin et al. ............. 600/454 |
| 5,488,953 | A | * | 2/1996 | Vilkomerson ............... 600/454 |
| 5,540,230 | A | * | 7/1996 | Vilkomerson ............... 600/454 |
| 5,738,097 | A | * | 4/1998 | Beach et al. ................ 600/455 |
| 6,176,829 | B1 | * | 1/2001 | Vilkomerson ............... 600/443 |
| 6,346,081 | B1 | * | 2/2002 | Vilkomerson ............... 600/454 |
| 6,535,835 | B1 | * | 3/2003 | Rubin et al. ................ 702/159 |

OTHER PUBLICATIONS

"Low–Cost Vector Doppler System Utilizing Diffraction-Grating Transducers", D. Vilkomerson et al., 2000 IEEE Ultrasonics Symposium, pp. 1491–1496.

"Redefined Duplex Ultrasonographic Criteria for Diagnosis of Carotid Artery Stenosis", John Houston III, MD et al., 2000 Mayo Foundation for Medical Education and Research, Mayo Clinic Proc, Nov. 2000, vol. 75, pp. 1133–1140.

"Doppler Ultrasound—Physics, Instrumentation and Signal Processing", second edition, David H. Evans et al., John Wiley & Sons, Ltd., pp. 150–155.

Abstract entitled, "Endarterectomy for Asymptomatic Carotid Artery Stenosis. Executive Committee for the Asymptomatic Carotid Atherosclerosis Study", The Journal of American Medical Association, vol. 273, No. 18, May 10, 1995.

* cited by examiner

Primary Examiner—Francis J. Jaworski
Assistant Examiner—Ruby Jain
(74) Attorney, Agent, or Firm—Duane Morris LLP

(57) ABSTRACT

An apparatus and method for detecting the highest velocity of fluid flow with in a volume having multiple sources of fluid flow with different velocities. There are multiple pairs of receiving transducers arranged about a region wherein each transducer in a pair is positioned on the same axis with respect to the region. A transmitting transducer is positioned at the region to provide an output frequency signal, which frequency signal is transmitted to the fluid flow area volume. This causes Doppler shifted frequency signals to be reflected, with the Doppler shift being a function of the fluid flow velocity. Each of the receiving transducers receive the Doppler shifted signals. Signal processing means are responsive to the Doppler shifted signals and the original transmitted output frequency signal to process those signals to provide a velocity signal for each pair of transducers. One then selects the maximum velocity signal obtained from the pair. By obtaining the maximum velocity signal, one then knows the direction of the maximum fluid flow which is determined by the axis pair of receiving transducers are located on.

20 Claims, 6 Drawing Sheets

DOPPLER SIGNAL ON 3:$f3=V_x(1+\cos a) + V_z \sin a$; ON 4:$f4=V_z(1+\cos a)-V_x \sin a$
SOLVING: $V_x=(f3-f4)/2 \sin a$   $V_z=(f3+f4)/(2+2 \cos a)$
(a)                               (b)

(a) "CROSS-BEAM" VECTOR DOPPLER CONFIGURATION FROM TOP AND FROM THE SIDE (b), WITH THE SENSITIVE VOLUME SHOWN IN GRAY WITH A SINGLE VELOCITY VECTOR CROSSING IT.

VECTOR

PERFERRED EMBODIMENT OF THE NEW SCREENING CONFIGURATION FOR VECTOR DOPPLER

SCHEMATIC DIAGRAM OF ELECTRONIC CONFIGURATION OF OPERATION OF PERFERRED EMBODIMENT OF FIG. 3

ERROR WITH RELATIVE VELOCITY, X-AXIS AS A PERCENTAGE, AND ANGLE, Y-AXIS IN DEGREES, TO THE PLANE OF THE REFERENCE VELOCITY VECTOR

ANGLE-INDEPENDENT DOPPLER SYSTEM FOR SCREENING

PRIORITY FILING

This application claims the benefit of the earlier filing date, under 35 U.S.C. 119, of commonly assigned provisional patent application, Ser. No. 60/378,515 entitled "Angle-Independent Doppler System for Screening," filed on May 7, 2002.

FIELD OF INVENTION

The present invention relates to devices that utilize ultrasound to determine the direction and speed of a fluid flowing in a vessel, and more particularly to Doppler diagnostic medical systems and methods for measuring blood flow.

BACKGROUND OF THE INVENTION

Doppler ultrasound measurements of flow, widely used for blood flow measurement in medical applications, and for the measurement of other scattering fluids in industrial applications, depend upon the Doppler effect, whereby a scatterer produces a change in the frequency of the ultrasound that it scatters. This change in frequency is proportional to two unknown quantities: the absolute magnitude of the velocity vector characterizing the motion of the scatterer, and the angle between the velocity vector and the insonating beam.

By simultaneously making two Doppler measurements of a velocity whose vector is coplanar with the transducer using two beams at known angles to each other, the resulting Doppler equations (each of which contains the unknown quantities of absolute value V and angle in the plane θ) can be solved simultaneously to calculate the velocity and angle to the transducer of that vector.

Determining three vector components of velocity by means of multiple Doppler equations has also been discussed, for example, U.S. Pat. No. 5,738,097 issued to Beach et al, and as discussed in the referenced patents U.S. Pat. No. 5,488,953 and U.S. Pat. No. 5,540,230. These patents taught apparatus and methods useful for pulsed Doppler, rather than CW Doppler. For certain applications where skilled operators to interpret the image in order to place the sampling gate needed for pulsed Doppler are not available (as for primary care screening for disease), CW Doppler is desirable. U.S. Pat. No. 4,062,237, issued to Fox, utilizes crossed CW beams and multiple frequencies where pairs of transducers operate at different frequencies so as to set up a difference frequency standing wave in the region of interest (equivalent to sensitive volume in this disclosure) in order to detect a Doppler frequency.

The method of using multiple Doppler measurements to determine the vector components of the velocity has been used by Daigle (1974 Doctoral Dissertation, Colorado State University) (unpublished) and implemented in previous patents, such as U.S. Pat. No. 5,488,953 "Doppler Diffracting Transducer" and U.S. Pat. No. 5,540,230 entitled "Doppler Diffracting Transducer", both issued to Vilkomerson, the inventor herein. These patents, in addition to issued U.S. Pat. No. 6,346,081 ('081) entitled "Angle Independent Continuous Wave Doppler Device" have disclosed means and methods of using special transducers, known as diffraction-grating-transducers (DGTs), to generate the multiple beams needed to effect this method. U.S. Pat. Nos. 5,488,953 and 5,540,230 teach the use of these transducers for pulsed operation, and patent '081, incorporated herein by reference, describes using these transducers for continuous wave (CW) operation. CW operation is often desirable for medical and some industrial uses because CW operation does not require adjustment of a "sample gate" to define the spatial region in which the Doppler system will measure the velocity. Instead, the region where the beams overlap define the "sensitive region". Patent '081 describes how this sensitive region is determined for CW operation.

In application U.S. Ser. No. 10/164,446, by Vilkomerson, the inventor herein, which is incorporated herein by reference, a CW, angle-independent system that is orientation independent is taught. As shown in FIG. 1, taken from the referenced application, it utilizes three (or more) Doppler measurements arranged so that the measurements involve the three spatial components of velocity, i.e. $V_x$, $V_y$ and $V_z$. Once the three components are determined, the absolute velocity V can be calculated as equal to $\sqrt{(V_x^2+V_y^2+V_z^2)}$.

Using such a transducer is particularly desirable when measuring blood flow under the skin, where the orientation of the blood vessel is not obvious. With the transducer such as that shown in FIG. 1, the velocity will be accurately determined independently of the orientation, as was demonstrated experimentally in "Low-Cost Vector Doppler System Utilizing Diffraction-Grating Transducers", by Vilkomerson et al., *Proc. 2000 IEEE International Ultrasonics Symposium*, IEEE Press, Piscataway (2001). Details of an instrument are provided there by which the three independent Doppler frequency signals containing three corresponding unknown velocity components in three spatial dimensions, i.e. $V_x$, $V_y$, and $V_z$, are analyzed in order to obtain the velocity in terms of the three measured Doppler frequencies.

Shortcoming of present vector Doppler methods—This method works well when a single velocity vector is present, such as when an artery or a vein is examined. However, there is an important medical application of Doppler use where more than one blood vessel is present: examining the carotid bifurcation for the presence of significant stenosis there. It has been shown that if plaque at this area reduces the diameter of the carotid artery to 40% or less (a "60%+ stenosis"), the risk of a serious stroke over 5 years rises to over 10%, and removing that plaque by means of an operation, a carotid endarterectomy, reduces the risk by over 50% ("Endarterectomy for asymptomatic carotid stenosis". Journal of AMA 273:1421–8, 1995). When such a stenosis is present, the area of the carotid is reduced to 0.16 of its normal area, and so the velocity increases inversely proportionally to the area; this increase of velocity can be easily detected by the Doppler signal that arises from the stenosis. While Doppler has been shown to be very effective at finding these stenoses (see, for example, Huston J., et al, "Redefined duplex ultrasonographic criteria for diagnosis of carotid artery stenosis", *Mayo Clin Proc* 75:1133–1140 2000) screening for this condition has not taken place because of the expense and operator-dependence of conventional duplex Doppler studies of the carotid. If a simple Vector Doppler transcutaneous examination were practical, such screening could take place.

However, the method of Vector Doppler, as described by Daigle, and others does not give accurate answers when applied to the carotid bifurcation. To understand why, we take a simple example: the "crossed-beam" system shown in FIG. 2. In this configuration for Vector Doppler (see patent by Beach, et al., already referenced) a pair of transducers is on the x-axis and a pair on the y-axis. If moving blood, represented by a velocity vector, exists in the shaded area shown in the Figure, its components, $V_x$ and $V_y$ can be found from the Doppler frequencies as shown in FIG. 2. When the maximum component $V_x$ and $V_y$ is found (by simply subtracting the frequencies as shown), the square root of the sum of the squares will provide the maximum velocity.

When two velocity vectors are present in the sensitive region, as would be expected where the carotid bifurcates, the method described above fails. Assume two equal velocity vectors, of value 100 cm/sec being present, one velocity vector along the x-axis, and a second one along the y-axis; the x-axis pair of transducers will provide the proper velocity for the x-vector, and the y-axis pair for the y-vector. When the velocities are squared, summed, and square-rooted, however, the answer will be 141 cm/sec, i.e. the $\sqrt{2}$ times the true maximum velocity. The basic assumption of the conventional vector Doppler method, that the velocity can be found by finding the spatial components and vector summing, does not hold for multiple velocity vectors occurring simultaneously. These conventional vector Doppler methods cannot be used for the important medical need of carotid screening, given the anatomy of the carotid bifurcation and this shortcoming.

SUMMARY OF INVENTION

We describe here a new configuration of vector ultrasound Doppler with CW beams that has the important advantage of detecting the highest velocity in its "sensitive volume", even when multiple velocities are present in the sensitive volume—a situation that causes the vector Doppler systems previously disclosed to give incorrect results. The new configuration is particularly well suited for screening, i.e. searching for high velocities indicative of stenoses, in the carotid bifurcation region (where the anatomy of the bifurcation ensures the existence of multiple velocity vectors).

The new invention can utilize diffraction-grating transducers for the advantages described in pending application U.S. Ser. No. 10/116,446: their capability of changing the angle of the beam produced by a change in the driving frequency, or by changing the phase relation among the sub-grids of the diffraction-grating transducer, as described in the referenced patents. The new invention can also use physically angled transducers emitting beams at perpendicular angle to its face, as shown in FIG. 3. The descriptions that follow will show the physically-angled conventional transducers for ease of discussion; however, the diffraction-grating transducer can be understood to provide a superior alternative to the conventional transducer in the discussion of the invention that follows.

DETAILED DESCRIPTION OF THE FIGURES

Disclosed herein are configurations and methods of using diffraction-grating transducers (DGTs) and non-DGTs for CW Doppler measurements to provide accurate three-dimensional measurement of velocity of dynamic particles such as blood cells flowing through a lumen such as a blood vessel. These configurations are applicable for transcutaneous use, where a need exists for measuring the velocity without seeing the orientation of the vessel. What separates this invention from the previously described vector Doppler configurations and methods is this configuration's capability to detect the highest velocity in the configuration's sensitive volume when more than one velocity, such as would be found at the bifurcation of the carotid artery, is present in the sensitive volume.

Figure 3:
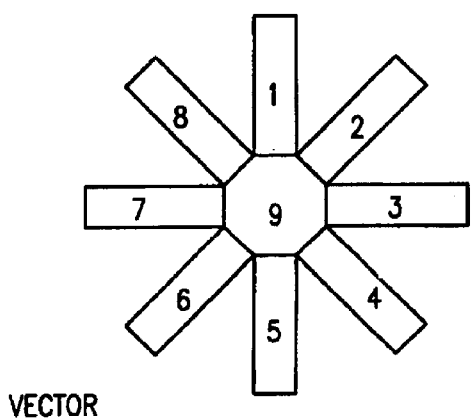
FIG. 3 shows the preferred embodiment of the new configuration designed for screening.

Referring now to FIG. 3, we see one version of the new configuration consists of multiple pairs of transducers arrayed symmetrically around a central transmitter. We can think of each of the four pairs, i.e. referring to the numbered transducers as pairs 1 through 5, 2 through 6, 3 through 7 and 4 through 8, as defining a set of four "sensitive axes". These axes are at 45° to each other.

Figure 1:
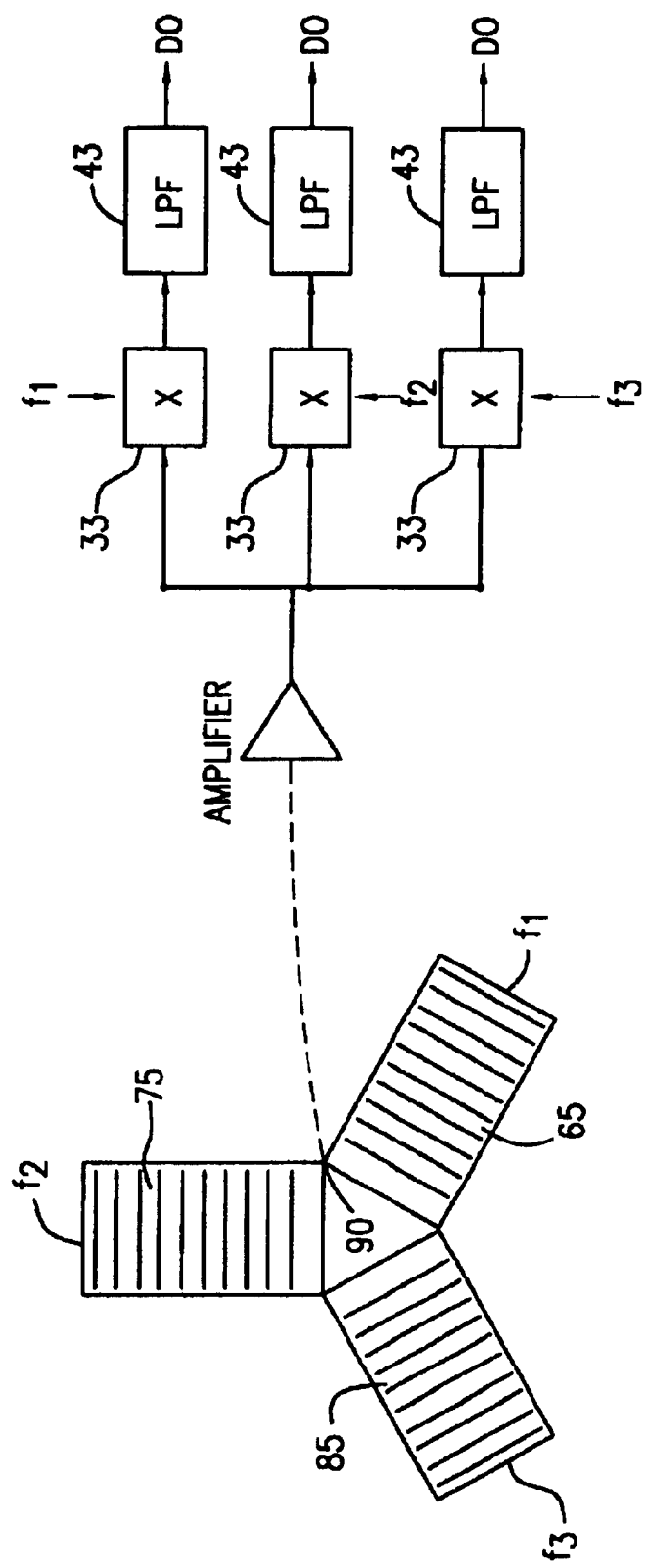
FIG. 1 provides an exemplary illustration of a conventional vector Doppler transducer configuration, taken from pending application U.S. Ser. No. 10/116,446.
Figure 2:
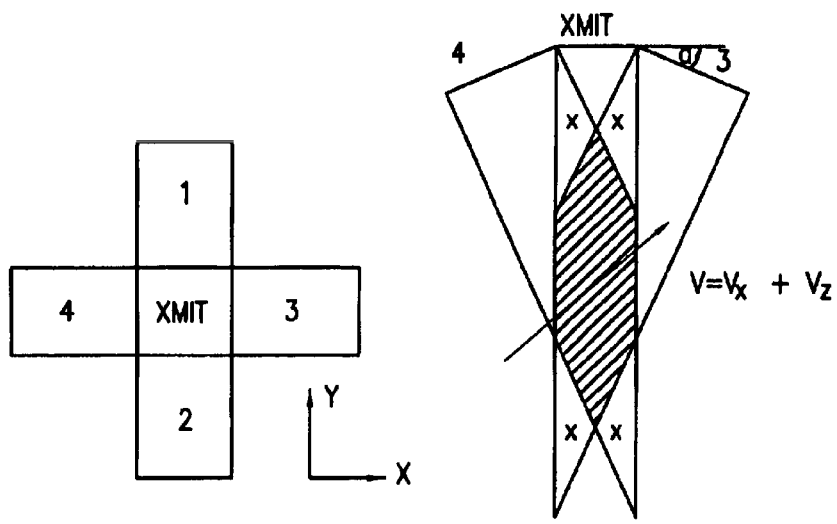
FIG. 2 provides an exemplary presentation of the operation of a conventional crossed-beam vector Doppler configuration, with a single velocity vector.
Figure 4:
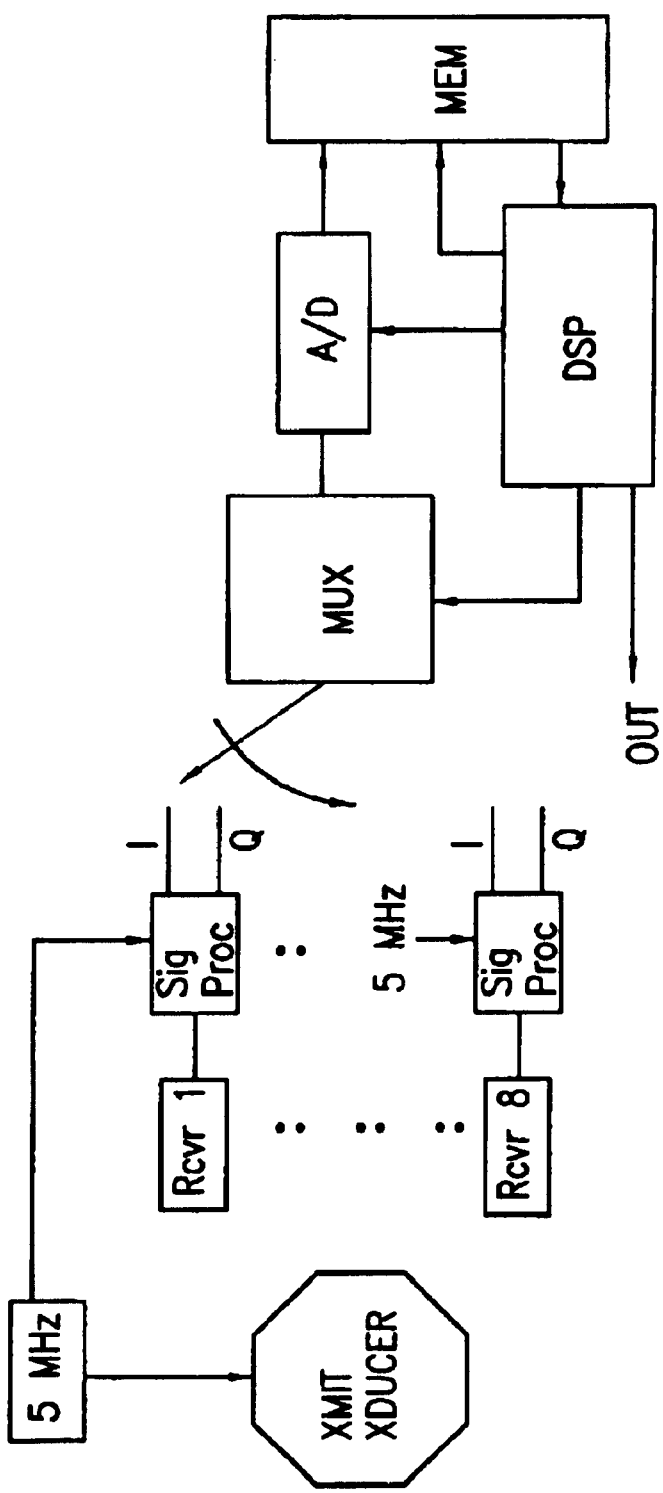
FIG. 4 shows a schematic representation of the electronic circuitry to be used in the preferred embodiment.

We can now take Doppler measurements, i.e. record the frequency shift ("Doppler shift") in the ultrasound backscattered by the blood caused by its velocity. As explained in the previously referenced materials, and is well-known to those skilled in the art, the Doppler shift is equal to the dot product of the velocity vector and the transmit beam vector, plus the dot product of the velocity vector and the receive beam, leading to the Doppler frequency shifts shown in FIG. 2 for that configuration. Here the central transducer, "9", transmits downward, and the Doppler-shifted frequency is measured on each receiving transducer. This can be done with the circuitry shown in FIG. 4. As shown there, in the box labeled "Sig Proc" the signal from each is amplified and heterodyned with the transmitting signal and a component of the same frequency but 90° phase; as is well-known, this produces the real and imaginary components of the Doppler shifted frequency known as the "I" and "Q" components. All 16 I & Q components can be measured by using a multiplexer ("MUX") to connect to each in turn at a rapid rate, with an A/D measuring the level of those, signals. As for example, using a 5 MHz transmitting signal, and a maximum velocity vector of 300 cm/sec, well above any normal velocity in the human body, Doppler shifts will be $\leq 10$ KHz. Therefore, the I & Q components must be sampled at least double that rate, or every 50 $\mu$S. If the multiplexer can switch channels and the A/D measure them in 1/16th of this period, i.e. or ~3.2 $\mu$S, all the I & Q channels can be sequentially "polled" every 50 $\mu$seconds. (The rate of change of blood velocity is much slower than this, so the delay between measuring the different signals will not affect the accuracy.) Such multiplexing-A/D units are readily available (the Linear Technology multiplexer-A/D IC that operates at 1.5 Megasamples/sec, i.e. every 0.6 $\mu$s, costs $6.00)

Figure 5:
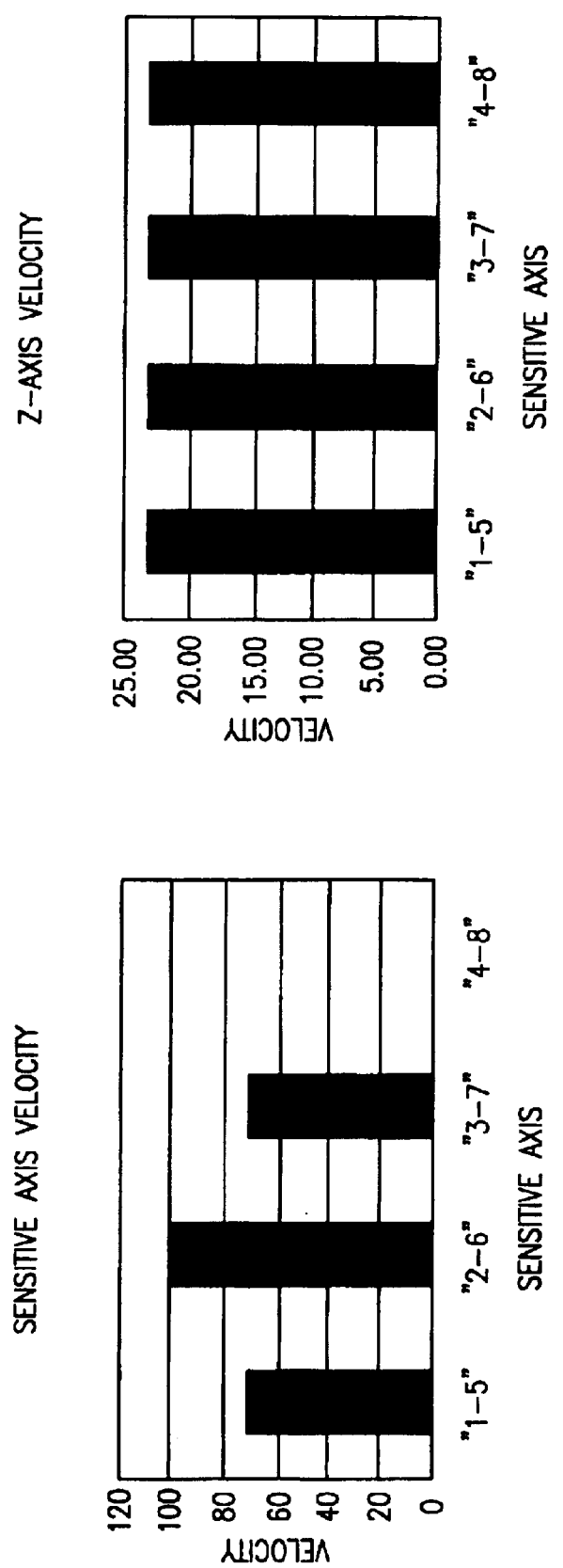
FIG. 5 shows the calculated velocities from the four different sensitive axes in the preferred embodiment when a single velocity vector is present in the sensitive volume.

The samples are Fourier-transformed to produce the Doppler shift from each transducer. (See, for example, *Doppler Ultrasound*, 2nd Edition, by Evans and McDicken, John Wiley Press, New York, 2000, (pages 112 through 114, 131 through 142, 155 through 155 and references) for details of how the Doppler information is extracted.) Then, the equations shown in FIG. 2, the sum and difference of the maximum Doppler frequencies from each pair on the four sensitive axes 1 through 5, 2 through 6, 3 through 7 and 4 through 8, are calculated. When the calculations are finished, the calculations will give results for a single velocity vector like those shown in FIG. 5: all the $V_z$ values will be the same (as a z-axis component will affect all the beams) and the different sensitive axis results will show one axis as higher than the others, which is the axis along which the velocity vector is best aligned. It the velocity vector happened to lie exactly between two sensitive axes, there could be two maxima, with value compared to the true value of 1−cos 22.5°, or 7.4%. Note that the sensitive axes at 45° to the one nearest the velocity vector show the cos 45° of the value of the true velocity, and the axis at 90° shows zero (the velocity vector is assumed to lie directly on the 2 through 6 axis, so the 4 through 8 axis is perpendicular to the velocity vector.

Figure 6:
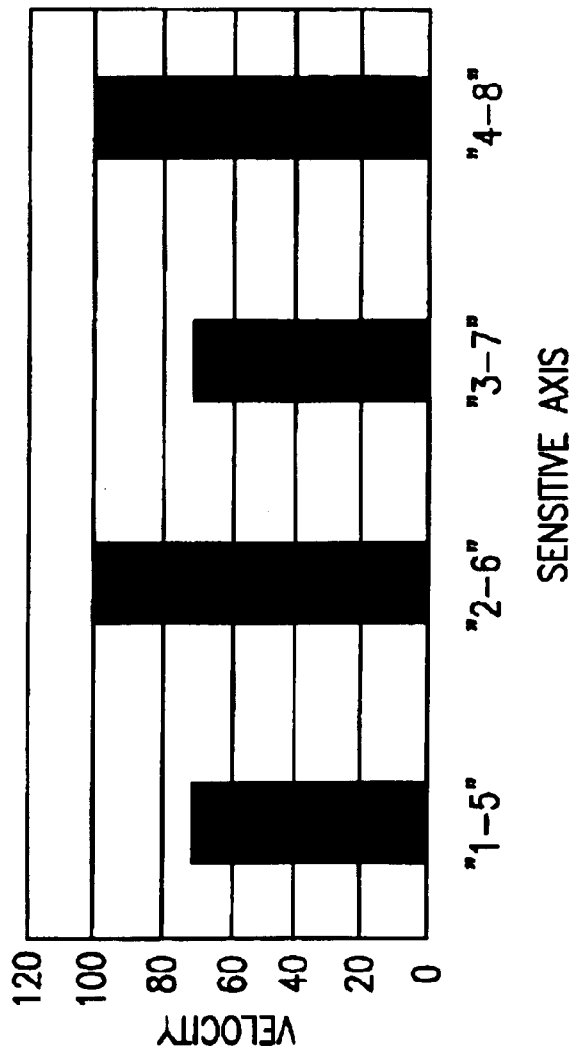
FIG. 6 shows the calculated velocities from the four different sensitive axes in the preferred embodiment when a single velocity vector is present in the sensitive volume.

FIG. 6 is an example of the same procedure when a second velocity, of value 0.9 of the first, is at 90° to it. In the conventional Doppler, the velocity would be calculated as 1.35 (taking the square root of the sum of the squares of the components). Here, the procedure is to take only the highest value, which is the correct 100 cm/sec.

There is one situation where this method can, give an incorrect result: if the second velocity vector is predominantly in the z-axis, it will determine the $V_z$ value, which as the total velocity includes the square root of the sum of the squares of the axis direction and $V_z$, can be incorrect.

This is unlikely for two reasons. Firstly, by comparing the ratio of $V_z$ to $V_{axis}$ over time, it will be clear that the $V_z$ component is not related to the $V_{axis}$ component, it being extremely improbable that the time behavior of two stenotic vessels (the kind that will have velocities high enough to be of interest in a screening examination) will be the same.

Figure 7:
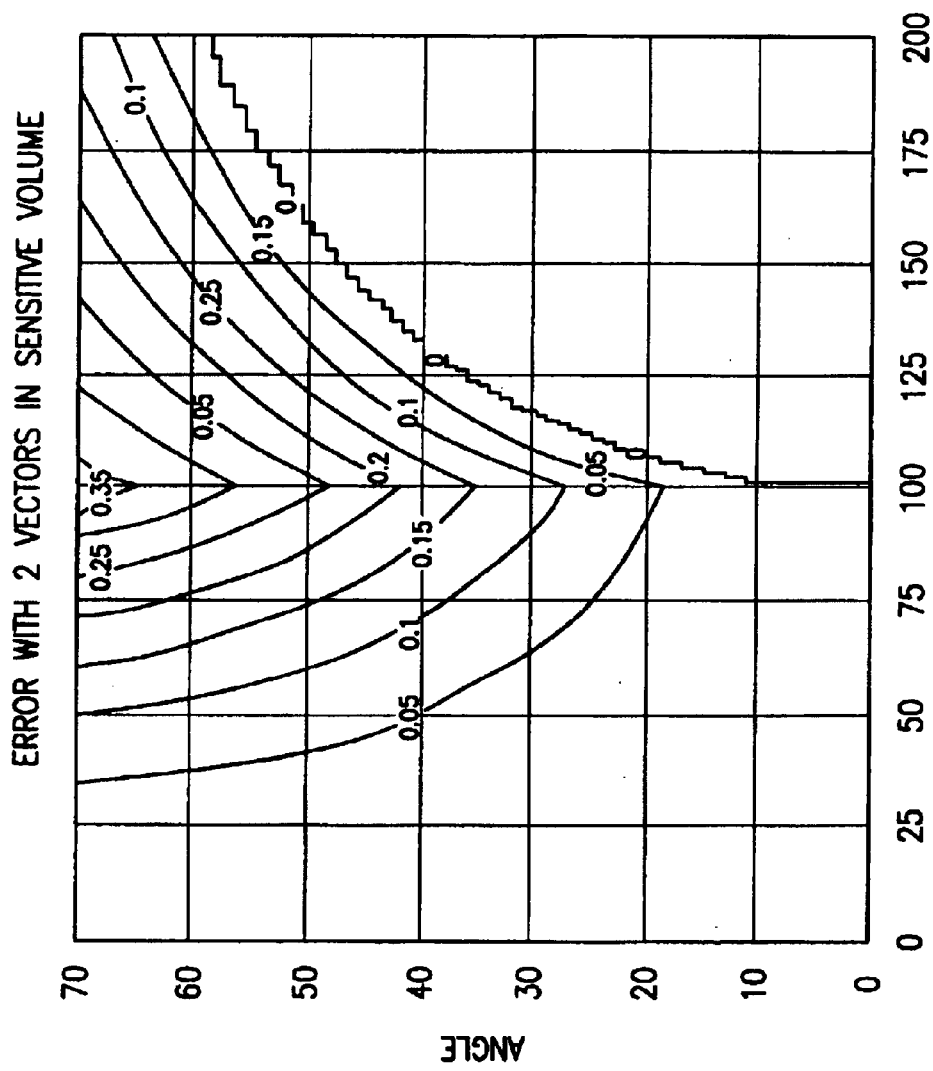
FIG. 7 shows the "contour map" of the relative error when a second velocity is present in the sensitive volume, as a function of relative velocity of the first to the second velocity, and of the angle of the second velocity out of the plane of the first velocity.

Secondly, as shown in FIG. 7, the range of relative velocities and angle between the two velocities that will cause significant error is small; note that only in the range above 50° and between 0.8 and 1.3 will the error ever exceed 25%. When the relative velocity is either much lower or much higher, the highest velocity will be determined. Further, anatomically, such a high angle between the two velocity vectors at the bifurcation is rare.)

Finally, there may be a situation where the system shows inconsistent $V_z$ values. This would be caused when velocity vectors are present "in the corners", i.e. in the regions marked "x" in FIG. 2. As they lie where only one of the side beams insonate them, such vectors will produce incorrect values using the sum and difference equations shown in FIG. 2, and inconsistent $V_z$ values as a result. In this case, the measurement is considered invalid, and the operator warned that an extraneous velocity is present. (Again, vessels in these areas are improbable for carotid screening, and the warning would prompt the operator to move away from them).

This same general method can be implemented with other numbers of transducers, e.g. if there are three sensitive axes at 60° intervals, utilizing six receivers around one transmitting transducer, somewhat less electronics and processing is required. The maximum error for this configuration when the vectors are approximately in the same plane (the most common anatomical configuration), is (1−cos 30°), i.e. the error found when the velocity is right at the edge of one of the sensitive axes detection region, halfway to the next sensitive axis, is 13.4%, as opposed to the 7.6% of the preferred embodiment. In general, the maximum error for n transducers arranged in pairs around the central axis is Maximum error=(1−cos[360°/2n]).

Thus for the preferred embodiment, with n=8, the maximum error is 7.6%, for n=4, 29.3%, or for n=10, 4.9%. The preferred embodiment is preferred because the accuracy is sufficient while the associated complexity of electronics is reasonable, but other numbers of transducers can be used with the tradeoff of accuracy for complexity inherent in the discussion above.

It is also possible to use an odd number of receivers, e.g. nine, and examine the Doppler shifts on opposing transducers to determine the "sensitive axis" defined between one receiver on one side of the central transmitter and two receivers on the other; by finding which transducer has the maximally different Doppler frequency, a synthetic sensitive axis is determined and the velocity determined therefrom. However, such a configuration has no advantage over the simpler to implement using even number of transducers.

Additionally, the transmitting transducer need not be in the center. As discussed in pending application U.S. Ser. No. 10/116,446, and illustrated in FIG. 5 of that application, the central area can remain open and one of the surrounding transducers used to insonate the area. For example, using the preferred embodiment of FIG. 3, but with no transducer 9, transducer 1 can be used as a sending transducer. The other transducers will receive Doppler shifts $f_n$ depending upon the angle of their sensitive axis, of (compare to the equation in FIG. 2).

$$f_n = V_z 2 \cos a + [\cos(\text{angle}_n°) + \sin a] V_{axis}$$

where $\text{angle}_n$ is the angle of the transducer being considered. Following the same polling of the Doppler shifts as with the other configuration, calculation will determine the axis along which the maximum velocity vector is present, but this configuration lacks the symmetry and ease of calculation of the central transducer configurations, and so is not preferred unless there is a need for access through the center. There are other configurations available to those skilled in the art that are combinations and variations of those discussed herein.

This invention is directed specifically to the need for screening, i.e. determining the highest velocity vector passing through a sensitive volume. It avoids the errors that occur in conventional vector Doppler when multiple velocity vectors in the plane cause the usual vector Doppler procedure of assuming the components of the velocity vector can be measured and then summed via the square root of the sum of the squares to give erroneous results. This invention results in a vector Doppler configuration that can be used for screening, in particular for the carotid bifurcation in which multiple velocity vectors are to be expected.

What is claimed is:

1. An apparatus for detecting the highest velocity of fluid flow within an area having multiple sources of fluid flow, each having a different fluid flow velocity, comprising:

multiple pairs of receiving transducers arranged about a region, wherein each transducer in a pair is positioned on the same axis with respect to said region, as the other transducer in said pair, with each pair positioned on a different axis about said region, a central transmitter transducer positioned at said region to provide an output frequency signal, which output frequency signal is transmitted to said fluid flow area to cause Doppler shifted frequency signals to reflect from said area with said Doppler shift a function of said fluid flow velocities, to cause each of said receiving transducers to receive said Doppler shifted signals, signal processing means responsive to said transmitted output frequency signal and each of said received Doppler shifted signals to provide a velocity signal for each pair of transducers, and means for selecting the largest velocity signal from said pairs which is indicative of the largest fluid flow and therefore, to select the direction of said largest fluid flow according to the axis upon which said pair of transducers is positioned.

2. The apparatus according to claim 1 wherein said region is a central region with said receiving transducer arranged symmetrically about said central region.

3. The apparatus according to claim 2 wherein each transducer is a diffraction grated transducer.

4. The apparatus according to claim 2 wherein said central area is an octagonal shape with a transducer positioned relatively central and extending radial from each side, with a pair of transducers defined by said transducers extending from opposite sides thereby forming a transducer pair, each pair on a separate axis separated from adjacent axes by 45 degrees.

5. The apparatus according to claim 2 wherein said central area is a symmetrical geometrical area such as a circle, hexagon, decagon and so on.

6. The apparatus according to claim 1 wherein said fluid flow area is located at the bifurcation of the carotid artery of a mammal.

7. The apparatus according to claim 1 wherein said signal processing means includes a heterodyne circuit responsive to the transmitted signal and a transmitted signal ninety degrees out of phase to heterodyne, these signals with the received signal for each transducer to provide at outputs an I and Q signal for each transducer, a converter for measuring the magnitude of each I and Q signals, a Fourier transform circuit responsive to said measured magnitudes to provide a Doppler shift signal for each transducer, a calculator for calculating a sum and difference signal for each pair of receiver transducers to provide a velocity signal for each pair, a selection circuit for selecting the largest velocity signal indicative of the direction of the largest fluid flow according to the axes of said selected pair.

8. The apparatus according to claim 1 wherein the number of receiving transducers is odd.

9. The apparatus according to claim 1 wherein the number of receiving transducers is even.

10. An apparatus for detecting the highest velocity of fluid flow within an area having multiple sources of fluid flow, each having a different fluid flow velocity, comprising:

multiple pairs of receiving transducers arranged symmetrically about a central region, wherein each transducer in a pair is positioned on the same axis through said central region as the other transducer in said pair, with each pair positioned on a different axis about said central region, a central transmitter transducer positioned at said central region to provide an output frequency signal, which output frequency signal is transmitted to said fluid flow area to cause Doppler shifted frequency signals to reflect from said area with said Doppler shift a function of said fluid flow velocities, to cause each of said receiving transducers to receive said Doppler shifted signals, signal processing means responsive to said transmitted output frequency signal and said received Doppler shifted signals from said transducers, to provide a real and (I) imaginary component (Q) of said received Doppler shifted signals for each receiving transducer, means for measuring said real and imaginary components of each transducer at a rate greater than that of any said fluid velocities to provide continuous samples for each transducer, means responsive to said samples to provide a Doppler shift for each transducer, means for calculating the sum and difference Doppler frequencies for each associated pair of transducers to obtain a single velocity value for each transducer pair, and means for selecting the highest velocity value for said pairs to define the direction and orientation of said highest velocity according to the direction of the axis on which said pair of transducers having said high velocity is positioned.

11. The apparatus according to claim 10 wherein said central region is octagonal in shape with a transducer positioned relatively central and extending radial from each side of said octagonal area, with a pair of transducers defined by transducers extending from opposite sides and on the same axis to form a transducer pair with said pair located on an axis separated 45 degrees from adjacent axes.

12. The apparatus according to claim 10 wherein said central region is of a symmetrical geometric shape as a circle, hexagon, decagon and so on.

13. The apparatus according to claim 1 wherein said fluid flow area is an area of the human body having multiple sources of blood flow such as at the bifurcation of the carotid artery.

14. A method for detecting the highest velocity of fluid flow within an area having multiple sources of fluid flow, each having a different fluid flow velocity, comprising the steps of:

placing a transmitting transducer above said area to transmit an output frequency signal to said area, surrounding said transmitting transducers with receiving transducers, said receiving transducers arranged in pairs about said transmitting transducer, each pair positioned on a common axis reserved for said pair, each receiving transducer receiving reflected Doppler shifted signals from said area, processing said received Doppler shifted signals according to said transmitted signals to provide a plurality of velocity signals from said transducers, selecting the maximum calculated velocity signal from a pair of said transducers as compared to the velocity signal of other pairs, and determining the direction of the flow of maximum velocity according to the axis upon which said pair is positioned.

15. The method according to claim 14 wherein said receiving transducers symmetrically surround said transmitting transducer.

16. The method according to claim 15 wherein receiving transducers are eight in number, thereby forming four pairs with each pair on opposite sides of said area and positioned on the same axis, with each pair of axes separated 45 degrees from another pair of axes.

17. The method according to claim 14 wherein the step of placing includes positioning the transmitting transducer above the carotid artier of a human.

18. The method according to claim 14 wherein said receiving transducers are diffraction grating transducers.

19. The method according to claim 14, including the step of surrounding said area with six receiving transducers, to provide three pair, each pair on opposite sides of a common axis through said region and separated by 60 degrees from adjacent axes.

20. The method according to claim 19 wherein said step of processing includes:

transforming said Doppler shifted signals by a Fourier transform to provide said Doppler velocity shift signals and calculating sum and difference frequencies for each pair to provide a velocity signal for each pair.

* * * * *